(12) United States Patent
Le (10) Patent No.: US 7,336,767 B1
(45) Date of Patent: Feb. 26, 2008

(54) BACK-SCATTERED X-RAY RADIATION ATTENUATION METHOD AND APPARATUS

(76) Inventor: Khai Minh Le, 5071 Audrey Dr., Huntington Beach, CA (US) 92649

(*) Notice: Subject to any disclaimer, the term of this patent is extended or adjusted under 35 U.S.C. 154(b) by 0 days.

(21) Appl. No.: 11/075,221

(22) Filed: Mar. 8, 2005

(51) Int. Cl.
*G21K 1/02* (2006.01)

(52) U.S. Cl. .................... 378/147; 378/149; 378/154; 250/363.1

(58) Field of Classification Search ............ 378/7, 378/19, 145, 147–155, 186; 250/267, 339.02, 250/363.05, 363.08, 397, 505.1, 363.1
See application file for complete search history.

(56) References Cited

U.S. PATENT DOCUMENTS

| | | | |
|---|---|---|---|
| 5,648,997 A * | 7/1997 | Chao | 378/98.4 |
| 5,949,850 A * | 9/1999 | Tang | 378/154 |
| 6,370,227 B1 * | 4/2002 | Guru et al. | 378/149 |
| 6,618,465 B2 * | 9/2003 | Mohr et al. | 378/58 |

FOREIGN PATENT DOCUMENTS

JP        04009146 A  *   1/1992

\* cited by examiner

*Primary Examiner*—Edward J. Glick
*Assistant Examiner*—Anastasia S. Midkiff
(74) *Attorney, Agent, or Firm*—William L. Chapin

(57) ABSTRACT

A method for improving resolution of X-ray radiography systems of the type used to obtain images of internal features of human bodies or to view contents of luggage articles, cargo containers and the like comprises positioning a plurality of baffle plates between the rear surface of an X-ray radiation detector array and a back stop used to limit transmitted X-ray radiation to a safe level. The baffle plates are made of a high atomic-number metal such as iron or lead which reduces by absorption, scattering or other attenuating processes the intensity of X-ray radiation back scattered from the back-stop onto the detector array, thus reducing noise contributions to signals output from detector elements of the array and thereby improving the quality of radiographic images formed from detector output signals. A back-scattered X-ray radiation attenuation apparatus according to the present invention utilizes pairs of horizontal upper and lower baffle plates disposed longitudinally rearward from upper and lower sides of individual X-ray radiation detector elements, or groups of elements, of a detector array, and optionally includes pairs of baffle plates disposed transversely to the horizontally disposed plates to thereby form an array of tubular collimator elements which intercept and attenuate X-ray radiation scattered from locations on a back-stop on lateral sides of as well as above and below the detector elements.

39 Claims, 7 Drawing Sheets

Fig. 1: Scattered radiation (Prior Art)

Fig 2: Scattered rays affect signal of transmission detector (Prior Art)

Fig 3: Collimation at detector to reduce influence of scatter (Prior Art)

Fig. 4: Back scatter corrupted transmitted signal (Prior Art)

Figure 5: Rear Collimator

Fig. 6: Rear collimator as parallel

Fig. 7: Rear collimator as a grid

Fig. 8: Rear collimator at back of detector

Fig. 9: Rear collimator at outside of back cover

Fig. 10: Rear collimator at outside of back cover

Fig. 11: Rear collimator at back wall

Fig. 12: Each rear collimator covers multiple detectors

Fig. 13: Arrangement for detector with wide gap

Fig.14: Rear collimator in line with X-ray beam

BACK-SCATTERED X-RAY RADIATION ATTENUATION METHOD AND APPARATUS

BACKGROUND OF THE INVENTION

A. Field of the Invention

The present invention relates to the field of X-ray radiography, in which ionizing radiation such as X-rays or gamma rays are used to form images of internal features of a human body, or of objects within luggage, shipping containers and the like. More particularly, the invention relates to a method and apparatus for reducing the intensity of X-rays back-scattered from backstops onto detectors used in X-ray radiography apparatus, thereby enhancing the signal-to-noise ratio and quality of radiographic images obtained by the apparatus.

B. Description of Background Art

Electromagnetic radiation of wavelengths substantially shorter than visible light, specifically X-rays and gamma rays having wavelengths less than about 0.1 nm, are routinely used to obtain visually discernible images of internal or sub-surface features of an object, by a method referred to as radiography. A widely used method of obtaining X-ray images, called transmission X-radiography, has been in use since shortly after the discovery of X-rays to obtain visual images of internal features of human bodies, such as bones and organs. Transmission X-ray radiographic images are created by exposing an X-ray sensitive device to X-ray radiation which has been transmitted through an object from a source of X-ray radiation. Historically, photographic film plates were among the first X-ray sensitive devices used for X-ray imaging, and are still widely used in the medical and dental fields. Transmission X-ray radiography systems using photographic film plates employ an X-ray source such as an X-ray tube which emits a beam of X-ray radiation. The X-ray beam, which typically has a conical or fan shape, irradiates an object field and a film plate holder located behind the object field. An object such as a human being or selected portion of the human's body is positioned in the object field between the X-ray source and the film plate holder, and upon being suitably positioned relative to the film plate holder and X-ray source, held stationary at that position. The X-ray source is then momentarily energized for a relative short, e.g., one-second time period which has been calculated to be just sufficiently long to form an adequate image in the emulsion of a photographic plate held in the plate holder. The exposure time is kept as short as possible because X-radiation has a cumulative destructive affect on biological cells. Therefore, the dosage energy, which is proportional to the product of X-ray intensity multiplied by exposure time, is desirably kept as small as possible.

Some X-ray radiation which irradiates an object such as a human body is transmitted with little attenuation, while rays which impinge on denser internal parts of the body, such as bone, are more heavily absorbed or scattered, thus forming in the emulsion of the photographic plate a shadow image of the denser object features. The film plate is developed and fixed by conventional film processing chemistry reactions and is kept as a permanent visual record for viewing and analysis by medical professionals. One variation of transmission X-radiography, called X-ray fluoroscopy, utilizes in place of a film holder, a screen which visibly fluoresces in response to X-radiation, enabling real-time dynamic viewing of internal object features.

Another variation of transmission X-radiography utilizes in place of a film plate or fluorescent screen a matrix array of photodetectors which are overlain by a fluorescent scintillator material that produces flashes of light or scintillations when irradiated by X-ray-radiation. Electrical signals output from the photodetectors are amplified and processed to form an electronic image of X-ray radiation incident upon the photodetectors. The electronic image can be converted to a visual image on a visual display device such as a cathode ray tube (CRT) or Liquid Crystal Display (LCD) display device of a television or computer monitor. The electronic image can also be input to a computer which uses display recognition software to automatically recognize contraband such as guns or explosive devices hidden in luggage examined by an X-ray radiography system.

To reduce the dosage of radiation on an object, some newer X-radiography systems uses a collimator made of an X-ray absorbing material such as steel, which has a slit-shaped aperture that deforms a conically-shaped X-ray beam into a relatively thin, vertically elongated, wedge-shaped fan beam of X-ray radiation. Such systems typically utilize a vertically disposed linear array consisting of one or more columns of scintillator-type X-ray detectors positioned at a detector plane located on the far side of an object field positioned between the collimated X-ray source and the target plane. A mechanism is used to cause the fan beam of X-ray radiation to horizontally scan the entire width or horizontal extent of an object to be imaged. One method for causing the fan beam of X-ray radiation to scan an object utilizes horizontal motion of the object, on a conveyor belt for example, to move the object relative to a fixed X-ray radiation source and detector array. Another scan method used in Computerized Axial Tomography (CAT) scanning utilizes rotation of the X-ray source and, synchronous orbital motion of the collimator and a flat or curved detector array, so that the beam remains at a fixed location on the detector array as the beam traverses the width of a stationary object located in the object field.

Whichever method is used to effect relative transverse motion between a fan beam of X-ray radiation on an object and a detector array, each instantaneous position of the beam on a particular column of detectors in the array produces detector output signals indicative of features in a single, narrow vertically disposed slice of the object. Thus, as the fan beam of X-ray radiation traverses the object and detector array, a sequence of electrical signals is output from the detectors. This sequence of output signals corresponding to a vertical stack of locations of an object, must be concatenated into a side-by-side arrangement of sequentially sampled vertical signal slices which represent a two-dimensional image of the object, or in the case of a CAT scan, a three-dimensional image of a human body.

Practical X-ray radiographic systems require a rather careful choice of X-ray energy levels used to image particular objects. Thus, the energy of X-ray radiation used to irradiate or illuminate an object to be imaged must be sufficiently large to penetrate denser features of an object. However, the X-ray energy levels should not be so large as to cause unneeded tissue damage to living subjects. Also, when high energy X-rays are required to penetrate and image dense objects such as cargo containers, vehicles, and the like, a problem can arise in using current X-ray radiographic systems for that purpose. That problem is scattered X-ray radiation which arises for reasons which will now be described.

When a beam of X-ray radiation impinges on matter, some of the X-ray photons are absorbed, and some are scattered, either in a forward direction, i.e., in the same direction as the incident beam, or backwards towards the source. Thus X-ray radiation having an energy of less than about 100 kV is typically absorbed by photo-electric absorption process. On the other hand, X-ray photons in the approximate energy range of about 100 KV to about MeV are elastically scattered by Thompson or Rayleigh scattering processes, or inelastically scattered by a Compton scattering process. For X-ray photon energies above about 1 MeV, the photons are absorbed by a pair-creation process in which electron-positron pairs are produced.

The absorption or scattering processes described above cause a beam of X-ray photons which impinges on a material object to be attenuated, thereby forming a shadow image of the object on a detector array positioned on an opposite side of the object from the X-ray beam source. The angles at which X-ray photons incident on atoms of the object are scattered, i.e., reflected or diffracted from an incident beam, depend on the material properties of the object and the angle of incidence. Moreover, X-ray photons which are inelastically scattered by the Compton scattering process undergo an energy loss. In a typical target object in which the arrangement of atoms is not uniform throughout the entire object, as they are in a single crystal, the scattered X-ray radiation often appears to be distributed in random directions. The effect can be visualized by shining a laser beam into a glass of water mixed with some milk, wherein light scattered in random directions from colloidal milk solids suspended in the solution cause the entire glass of solution to glow visibly when viewed from various directions.

Photons which are scattered in directions that have polar angles between plus and minus 90 degrees of the direction vector of an incident photo beam, i.e., those contained in a forward-facing hemisphere as viewed from a target and detector, are said to be forward scattered. Conversely, photons which have polar angles of 90 degrees to 180 degrees from the incident photon beam direction vector, i.e., those contained in a rearward-facing hemisphere, are said to be back-scattered. Both forward-scattered and back-scattered photons can degrade the quality of images obtained in X-ray radiographic systems, for reasons which will now be explained.

As described above, transmission X-ray radiographic systems utilize a source of X-ray radiation to irradiate or illuminate an object, and form an image of internal features of the object on a photographic film, fluoroscopic screen, or detector array. The image is formed as a result of more or less attenuation of incident X-ray radiation by more or less dense object features, thus causing fewer or more X-ray photons to impinge on a detector array plane and thereby resulting in an image having darker and lighter contrasting features, as manifested by fewer or more detected photons in the darker and lighter areas of the image. Therefore, it can be readily appreciated that X-ray photons which impinge on a detector from a location that is not on a common axis which joins a particular detector element to the source of X-ray radiation which illuminates an object feature, do not characterize the object featured, and therefore constitute noise, rather than a useful signal. Such noise signals will degrade the quality of an image formed using the signal detector output.

For example, since practical X-ray radiographic systems utilizing a conically-shaped flood beam or a wedge-shaped fan beam of X-ray radiation to illuminate an object to be imaged, there are in addition to a narrow bundle of rays which lie in a pencil beam along an optical axis between the X-ray radiation source and a particular detector, a significant number of off-axis rays which angle away from the optical axis and therefore irradiate object features other than the one aligned with the particular detector. Off-axis object features can forward-scatter off-axis X-ray radiation beams into a particular detector which defines an instant optical axis. The forward scattered rays which impinge upon that detector do not characterize an object feature on the instant optical axis defined by that detector, and therefore, produce image-degrading noise signals in that detector. The noise signals result in image degradation which can reduce discernability of dense image features. Signal-to-noise degradation caused by forward-scattered X-ray radiation is particularly acute when imaging dense objects. This is because the intensity of X-ray radiation transmitted through dense objects is inherently small, resulting in small detector signals, which can more readily be overwhelmed by noise signals produced by forward-scattered X-ray radiation.

To reduce the deleterious effects of forward-scattered X-ray radiation on detector signal-to-noise ratios and image quality, some high-end X-ray radiography systems such as computerized axial tomographic (CAT-Scan) systems employ an individual collimator positioned at the front of each X-ray radiation detector used in the imaging system. The collimators are typically constructed as tubes made of a dense, high atomic number (high-Z) material such as lead, positioned in front of and in axial alignment with individual detectors. Such collimators function as individual lens hoods or baffle tubes for each detector.

In certain X-ray radiography systems, the X-ray radiation source energy levels, detector thickness, and other parameters are chosen so that virtually all incident X-ray radiation is captured by the detectors. Therefore, in such systems, there is typically very little X-ray radiation which is able to bypass or leak through the scintillation detectors and reach the back wall of a detector box in which the detectors are located. Thus back-scattered X-ray radiation is usually not a problem in such systems. Back-scattered X-ray radiation is, however, problematic in high-energy X-ray radiography imaging systems, as will now be described.

In high-energy, high dosage X-ray radiography imaging systems, because of high material costs and other practical considerations, it is usually impractical to fabricate detectors with sufficient thickness to absorb all or most X-ray radiation incident upon the detectors. Therefore, detector arrays used in typical high-energy X-ray systems allow 30% to 40% of incident X-ray radiation to be transmitted through the detectors. Such systems are usually constructed so that the errant X-ray radiation which is transmitted through the detectors strikes a back-stop wall positioned behind the detector chamber, but some of that radiation is unavoidably scattered back towards the detectors.

In compact X-ray radiography systems, the back-stop wall is usually made of steel or lead which has a thickness sufficient to reduce the intensity of X-ray radiation that escapes from the detector chamber to a reasonably safe level. In large, fixed-site X-ray radiography systems, the back wall is typically made of concrete.

To reduce the effect of errant X-ray radiation which is back-scattered from a back wall towards the detectors, typical systems are designed with the back wall located many meters rearward of the detectors. There are, however, a variety of situations in which back-scattered X-ray radiation can impinge on X-ray detectors in a manner which causes significant degradation of the signal-to-noise ratio of detector output signals, resulting in significantly degraded images of object features obtained using the detectors, as will now be explained.

As described above, typical transmission radiography systems used to form images of internal features of an object utilize multiple detectors arranged in an array, which generally has a rectangular shape. The detector array is positioned some distance behind an object field containing an object, and the object field is positioned some distance behind a source of X-ray radiation, which typically illuminates the object field with a conically-shaped beam, or a wedge-shaped fan beam. Different parts of an object positioned in or passing through the object field may have very large variations in density, and therefore, in X-ray absorption or transmission characteristics. For example, in forming an X-ray radiography image of an automobile or other motor vehicle, X-ray radiation which passes through an engine block will be highly attenuated, while X-ray radiation which travels through open windows of the vehicle will be minimally attenuated.

Obviously, rays of X-ray radiation which have been transmitted through dense object features such as an engine block will retain a very small portion of incident intensity when impinging on a detector. Such rays will therefore result in very little energy being transmitted through the detector, and therefore will cause minimal back-scattered radiation from the back wall of the radiography site. However, incident X-ray radiation beams which are transmitted through low-density regions of the object will retain much of their energy when incident upon the detectors. Thus, even though some attenuation of these high energy rays occurs in the detector, a substantial portion of the energy is retained to impinge on the back wall. Back-scattered radiation produced in the back wall material from these relative high energy rays which have "leaked through" the detector can impinge on the rear surfaces of adjacent detectors, as well as the detector or detectors through which the radiation leaked. And, since the scintillator layer in each X-ray radiation detector produces a light scintillation regardless of the source direction of the X-ray photons on the scintillator layer, the photo-detector optically coupled to the scintillator layer of X-ray radiation detectors irradiated by scattered X-rays produces output signals which do not represent object information, and therefore constitute noise. That noise signal detracts from signals representing object information, therefore degrading the signal-to-noise ratio of signals output from detectors, for example, which are irradiated by back-scattered radiation emanating from a back-stop wall.

The present invention was conceived of to provide a method and apparatus for reducing the intensity of X-ray radiation back-scattered onto X-ray radiation detectors, to thereby reduce noise signals output from the detectors, improve signal-to-noise ratio, and enhance contrast ratio and detail resolution of images formed in X-ray radiation radiography systems.

OBJECTS OF THE INVENTION

An object of the invention is to provide a method and apparatus for attenuating X-ray radiation which is scattered from a location other than that of an object feature being imaged by an X-ray radiography system and impinging on a X-ray radiation detector used to image the feature, the scattered radiation constituting image-degrading noise.

Another object of the invention is to provide a method and apparatus for reducing the intensity of errant back-scattered X-ray radiation which impinges upon detectors used in an X-ray radiography system.

Another object of the invention is to provide a method and apparatus for use in X-ray radiography systems to reduce the intensity of X-ray radiation back-scattered from a back-stop onto detectors used in the system.

Another object of the invention is to provide a method and apparatus for reducing back-scatter of X-ray radiation into X-ray radiation detectors used in a transmission X-ray radiography system.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends a method and apparatus for improving the performance of X-ray radiography systems of the type which are used to form images of internal features of objects such as internal organs of human patients, or of objects contained within articles of luggage or cargo containers. The method and apparatus according to the present invention are particularly well suited to use with transmission X-ray radiography systems of various types, including those used in CAT-scan systems to obtain images of internal features of human bodies, and those used to view the contents of luggage pieces, cargo containers and the like.

According to a basic aspect of a method and apparatus for reducing the deleterious effects of back-scattered X-ray radiation onto detectors used in X-ray radiography systems, X-ray attenuating baffle plates made of a high-Z (atomic number) material such as lead or steel are positioned behind X-ray radiation detectors, and in front of a source of back-scattered radiation, such as a back-stop wall. The baffle plates are preferably configured as an array of vertically or horizontally orientated plates, or a combination of both vertical and horizontal plates arranged to form a rectangular grid. The geometrical configuration of the baffle plates is arranged so that a significant portion of beams of X-ray photons back-scattered from a back-stop of an X-ray radiography apparatus is intercepted and attenuated by absorption, scattering, or other processes occurring in the baffle plates.

A basic embodiment of a method and apparatus for attenuating back-scattered X-ray radiation beams according to the present invention includes positioning a pair of generally longitudinally disposed, vertically spaced apart horizontal metal plates rearward of an X-ray radiation detector, directed towards a back-stop. For a spacing between plates equal to a detector element height d and a plate length rearward of the detector 1, the vertical acceptance angle or angle of view V at the center of the detector, looking rearward, is given by 2 arctangent $(d/2l)$. Thus, all rays of X-ray radiation back-scattered from a back-stop towards a detector which emanate from locations on the back-stop above or below the center line or optical axes of the detector sufficiently far for the incident angle at the center of the rear face of the detector to exceed the angle V/2 are intercepted by the upper or lower baffle plates, respectively.

Since even relatively modest ratios of baffle plate length to spacing between the plates yields angles V which are substantially less than 180 degrees, the ratio of unattenuated back-scattered X-rays receivable by a detector provided with baffle plates to that receivable by a detector that is not provided with baffle plates is substantially reduced to the ratio (V÷180). Thus, a pair of baffle plates used according to the present invention as described above to limit the acceptance angle of an X-ray radiation detector for back-scattered X-ray radiation functions as a lens hood or single-axis collimator.

To further reduce the amount of unattenuated back-scattered X-ray radiation receivable from a back-stop by a detector, the horizontal acceptance angle for back-scattered rays may be reduced by a pair of vertically disposed, horizontally spaced apart metal baffle plates which protrude rearwardly from opposite vertical sides of a detector, forming with the horizontal plates a rectangular elevation-view tube, or two-axis collimator.

To attenuate X-ray radiation back-scattered onto a vertical column of detectors by the method of the present invention, a stack of vertically spaced apart horizontal plates may be positioned rearward of the column, in a manner exactly analogous to the deployment of two plates for use with a single detector according to the basic embodiment of the invention described above. Also, according to the present invention, a stack of horizontally spaced apart vertical baffle plates may be combined with a stack of horizontal plates into a rectangular "egg-crate" grid or lattice for attenuating rays back-scattered from locations on the sides of the detectors. Both single-axis and two-axis collimators can be used with detector arrays having multiple vertical columns of detectors.

As described above, a basic embodiment of the present invention comprises a pair of metal baffle plates which protrude rearwardly from each X-ray radiation detector towards a back-stop, to thereby attenuate X-ray radiation which is back-scattered from the back-stop towards the detector. In a first variation of the basic embodiment, rearwardly facing baffle plates deployed towards the back-stop are attached to a separate support structure which is spaced rearwardly from the detectors. A second variation of the invention has baffle plates of the type described which protrude forwards towards the detectors from a support structure located rearward of the detectors.

In a third variation of a back-scatter radiation attenuation apparatus according to the present invention, radiation attenuating baffle plates of the type described above are mounted close to or directly on a back-stop, protruding towards a detector array.

For use with detector arrays in which there are gaps of significant size between adjacent detectors in an array, a preferred embodiment of the present invention utilizes baffle plates which are longitudinally aligned with detector elements. This arrangement ensures that X-ray radiation beams that pass through gaps between detector elements do not impinge directly on the facing edge of a baffle plate, which itself would then become a strong back-scatter site. By offsetting the baffle plates from axial alignment with gaps between the detectors and aligning the front edges of the baffle plates with the detectors, beams of X-ray photons which are not attenuated by passing through a detector element travel towards the back-stop between baffle plates, which result in back-scattered X-ray radiation beams that are attenuated by the baffle plates.

According to another aspect of the invention, for use with detector arrays in which normal axes of individual detector elements are inclined with respect to one another, baffle plates are oriented so that upper and lower surfaces of each plate are parallel to upper and lower edges of the detector element, with a rearward extension of the optical axis of a detector lying within the plane of the detector elements. This arrangement helps to insure that X-ray radiation rays that pass through the detector array travel rearward to the back-stop in a direction generally parallel to baffle plates towards the back-stop.

DESCRIPTION OF THE PREFERRED EMBODIMENTS

Figure 13:
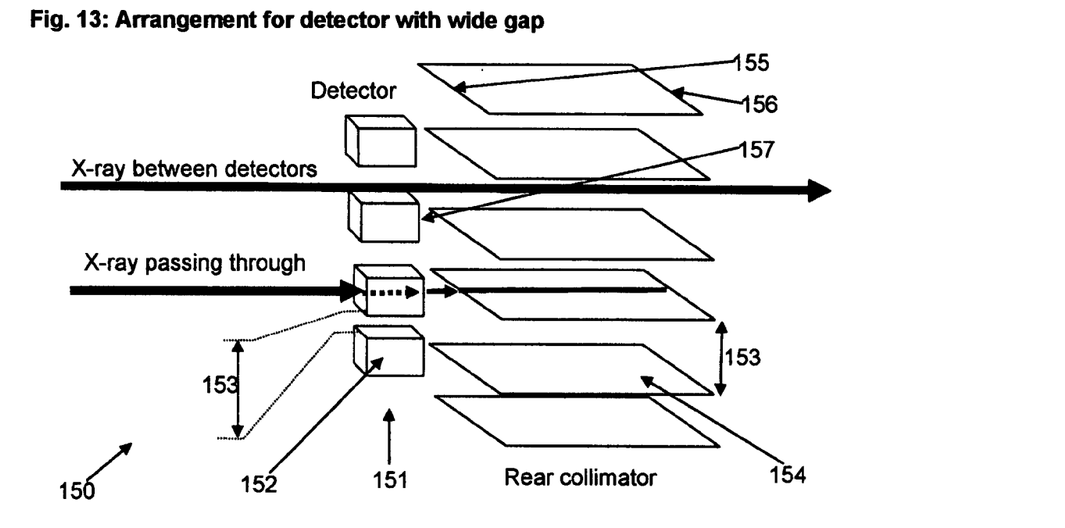
FIG. 13 is a diagrammatic view showing a preferred arrangement of rear collimator baffle plates for use with gapped detector arrays according to the present invention.
Figure 14:
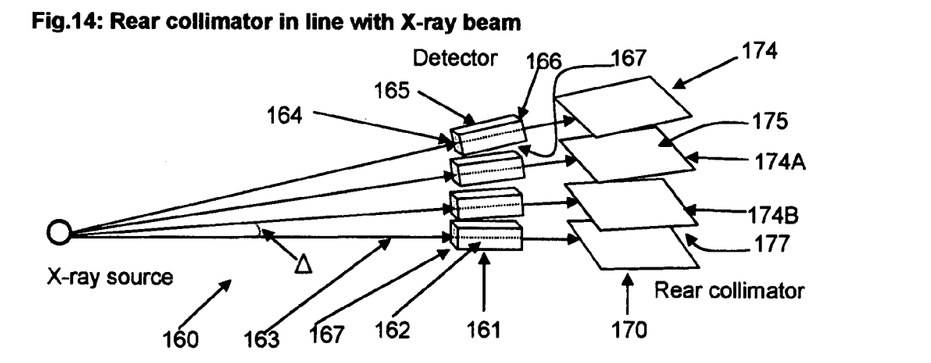
FIG. 14 is a diagrammatic view showing a preferred arrangement of collimator baffle plates according to the present invention for use with detector arrays in which the normal axes of individual detector elements of the array are angled with respect to one another.

FIG. 14 illustrate geometrical relationships between X-ray radiation beams in prior art transmission X-ray radiography systems which give rise to image degradation caused by X-ray radiation back-scattered onto X-ray radiation detectors used to form an image of an object. FIGS. 5-14 illustrate various aspects of methods and apparatus according to the present invention for reducing back-scattered X-ray radiation incident upon detectors.

Figure 1:
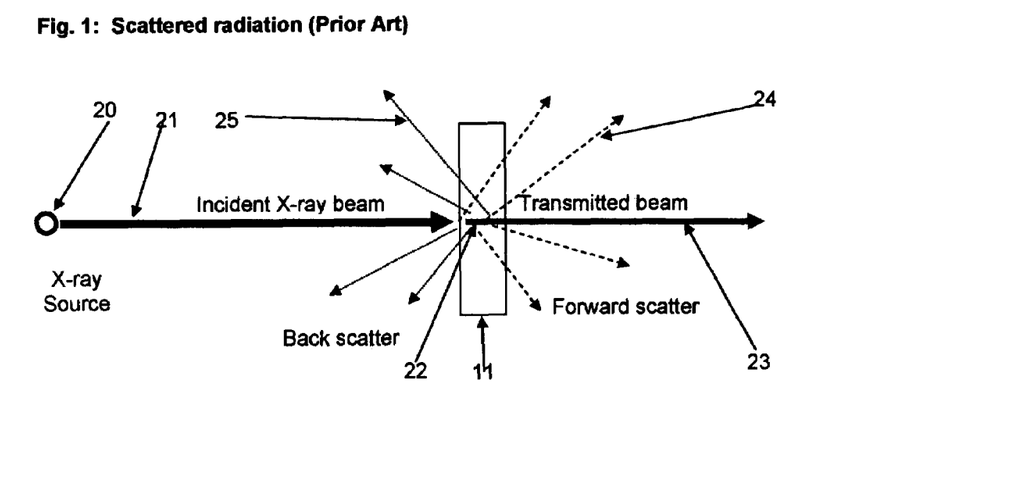
FIG. 1 is a schematic diagram showing relationships in a typical prior art X-ray apparatus between an X-ray radiation beam incident upon a material object, and rays of transmitted, forward-scattered and back-scattered photons produced by interaction of the incident beam with atoms of the object.

Referring first to FIG. 1, an X-ray radiation source 20 is shown emitting a beam of X-ray photons 21 which are incident upon the front surface of a target object 11. Incident beam 21 collides with atoms 22 within target object 11, resulting in absorption of a portion of the incident beam, thus resulting in a transmitted beam 23 of reduced intensity that exits from a rear surface of the target object. Some collisions of X-ray photons in incident beam 21 with atoms 22 of target object 11 result in forward scattered X-ray photons 24 which have direction vectors confined to a hemisphere facing forward from the rear surface of the target object, and back-scattered X-ray photons 25 which have direction vectors confined to a hemisphere facing rearward from the front surface of the target object.

Figure 2:
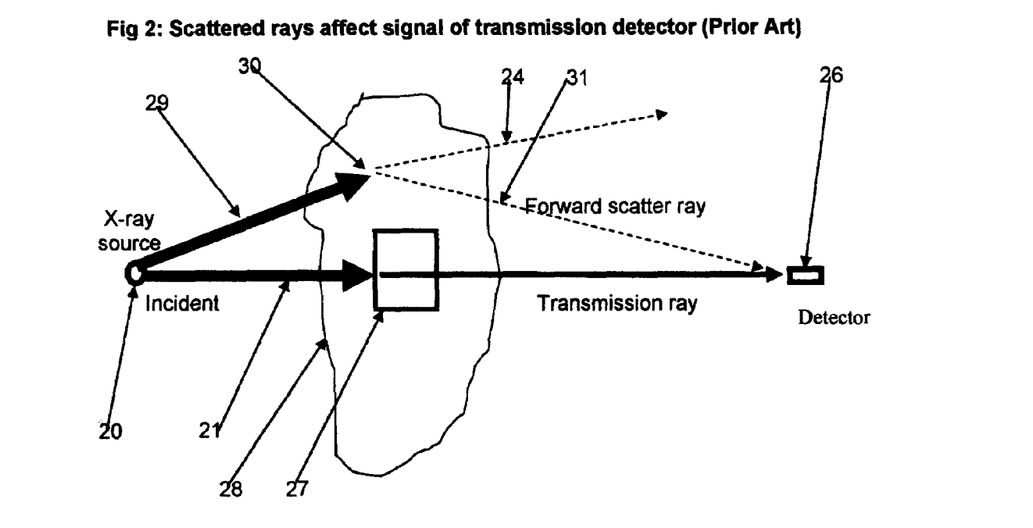
FIG. 2 is a simplified schematic view showing spatial relationships between incident and forward-scattered X-ray photon beams in a prior-art transmission radiography apparatus.

FIG. 2 is a fragmentary diagrammatic view of a prior-art transmission X-ray radiography system, in which forward-scattered X-ray radiation can degrade an image obtained of an object. Thus, as shown in FIG. 2, X-ray radiation source 20 emits a beam 21 of X-ray radiation aligned with a detector 26 which is incident upon an internal feature 27 of a target object 28. X-ray radiation source 20 also emits off-axis rays such as ray 29 which are angled with respect to an axis defined by a straight line that is directed between the source and detector 26. Off-axis ray 29 impinges on an object area 30 different from on-axis feature 27, thereby producing forward-scattered X-ray radiation beams 24, which include rays such as ray that can impinge upon detector 26. Since forward-scattered ray 31 does not represent characteristics of that portion of internal feature 27 axially aligned with X-ray radiation source 20, signals output from detector 26 in response to the errant off-axis ray 31 constitute a noise signal which degrades the signal-to-noise ratio of the detector output, and thus of any image formed using the output signal.

Figure 3:
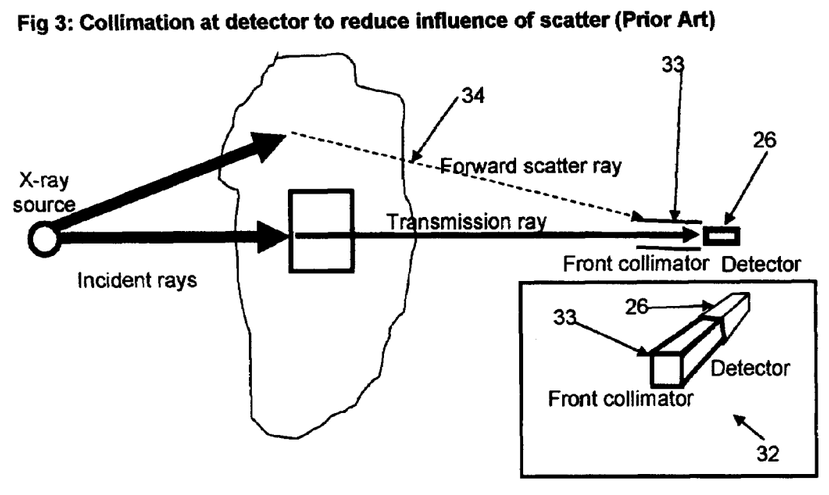
FIG. 3 is a view similar to FIG. 2 but showing a modified prior-art X-ray radiography apparatus which includes a front collimator positioned in front of an X-ray radiation detector to reduce the intensity of forward-scattered X-ray radiation beams on a detector.

FIG. 3 illustrates a prior-art arrangement for reducing the intensity of forward-scattered X-ray radiation onto an X-ray detector. As shown in FIG. 3, prior art apparatus 32 utilizes a tubular collimator 33 made of a dense metal such as lead or steel, which is positioned in front of a detector 26 to thereby limit the angle of view of the detector surface to a value less than hemisphere, i.e., less than 2 π steradians, and thereby limit the area of the object from which forward-scattered X-ray-ray beams, such as ray 34 in FIG. 3, can impinge upon detector 26.

Figure 4:
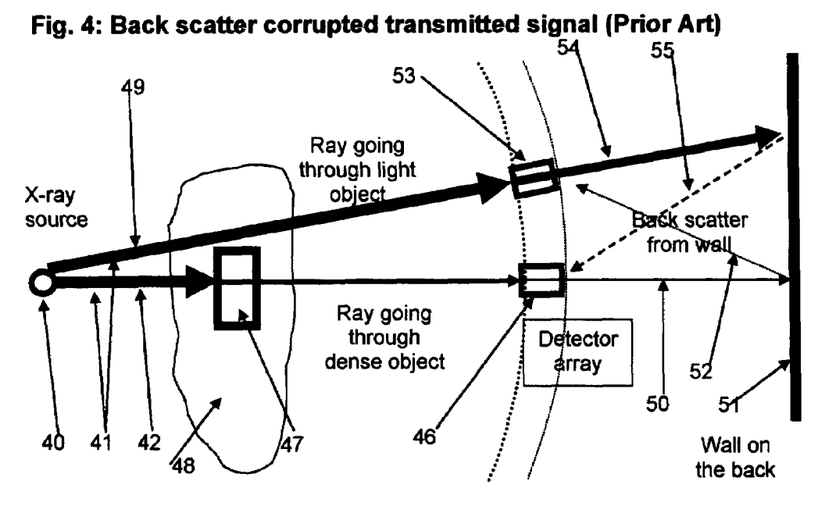
FIG. 4 is a simplified schematic view of a prior-art transmission X-ray radiography apparatus showing spatial relationships between an incident X-ray photon beam and X-ray photon beams back-scattered towards a detector from a back-stop located behind the detector.

FIG. 4 is a fragmentary diagrammatic view of a prior-art transmission X-ray radiography system, in which X-ray radiation back-scattered from a back-stop behind a detector array can degrade imaging performance of the system.

Referring still to FIG. 4, an X-ray radiation source 40 emits a beam 41 of X-ray radiation which includes a ray 42 that is axially aligned with an internal feature 47 of a target object 48 and a detector 46. Beam 41 of incident X-ray radiation also includes off-axis rays, such as ray 49, which are emitted simultaneously with on-axis ray 42, in a typical case where beam 41 is a conically-shaped flood beam or a wedge-shaped fan beam, or subsequently to the emission of beam 42, if beam 41 is a scanning pencil beam of radiation.

As shown in FIG. 4, on-axis beam 42 is initially attenuated by absorption and/or scattering by internal feature 47 of target object 48, and subsequently attenuated further by detector 46. Therefore, a ray 50 which is transmitted through detector 46 and strikes a protective back-stop wall 51 is of relatively low intensity. Accordingly, rays 52 back-scattered from back-stop wall 51 after having passed through a detector such as detector 46 have a relatively low intensity. On the other hand, rays such as ray 49 which travel through less dense regions of target object 48, e.g., an open passage compartment of a vehicle as opposed to an engine block, experience little or no attenuation in traveling through the target object. For that reason, a ray such as ray 49 which is incident upon detector element 53 emerges as a transmitted beam 54 with little attenuation and thus produces a relatively intense ray 55 back-scattered from back-stop wall 51. If ray 49 is not intersected by a detector element 53, the ray experiences even less attenuation and therefore causes an even larger noise signal to be generated in detector 46.

Figure 5:
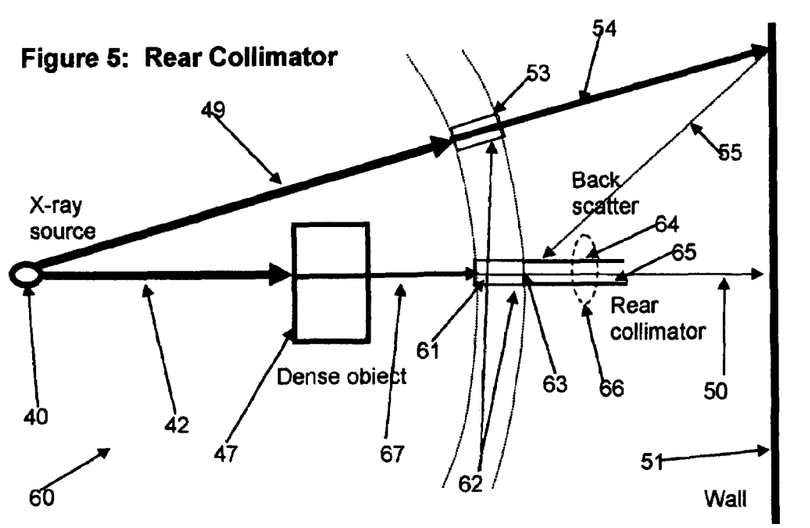
FIG. 5 is a diagrammatic view of a basic embodiment of a method and apparatus according to the present invention for reducing the intensity of X-ray radiation back-scattered onto a detector of an X-ray radiography system.

FIG. 5 is a diagrammatic view of a basic embodiment of a method and apparatus according to the present invention for reducing the intensity of X-ray radiation back-scattered onto detectors of an X-ray radiography system.

Figure 6:
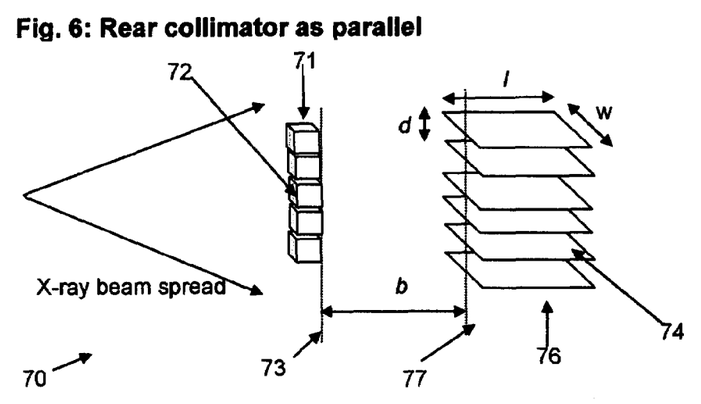
FIG. 6 is a partly diagrammatic perspective view showing an array of parallel baffle plates arranged to form a back-scatter attenuating, vertical, single axis collimator for a detector array comprising one or more adjacent vertical columns of individual detector elements.

As shown in FIG. 5, an embodiment 60 of a back-scatter attenuator apparatus according to the present invention includes a pair of parallel, upper and lower baffle plates or collimator plates 64, 65, respectively, which protrude from a rear surface 63 of a detector element 61 of a detector array 62. As will be explained in further detail below, baffle plates 64, may have a length I rearward from the detector of 64, of different values depend on desired performance parameters. Also, baffle plates 64, 65 may have different widths w (perpendicular to the page in FIG. 5, as indicated in FIG. 6), but preferably have a width at least as great as that of detector element 62.

Upper and lower baffle plates 64, 65 cooperate to comprise a single-axis rear collimator 66. The baffle plates 64, 65 are preferably made of a material which has significantly high absorption characteristics for X-ray radiation having energies in the range emitted by X-ray radiation source 40. Therefore, collimator baffle plates 64, 65 are typically made of materials composed of a high atomic number (high-Z) elements, such as lead or steel. Although the thickness, length and width dimensions of baffle plates 64, 65 are a matter of design choice, provided that they meet the functional criteria set forth here, the plates would typically be made of steel or lead and have a thickness sufficient to result in significant attenuation of X-rays in the particular energy range used in a system.

Referring to FIG. 5, it can be understood that, in the absence of rear collimator 66, X-ray photons 55 back-scattered towards detector array 62 from any location of back-stop could impinge upon detectors 61 of the array. Thus, the polar acceptance angle of back-scattered photons by a detector 61 not provided with a rear collimator 66 according to the present invention could be as large as 180 degrees. FIG. 5 shows only a vertical slice of a rearward facing hemisphere from which a "bare" detector 61 could receive back-scattered photons, but is can be appreciated that the detector could receive back-scattered photons which have direction vectors with different azimuthal angles pointing to any location lying on a hemisphere centered on the detector, i.e., over a sold angle of $2\pi$ Steradians.

However, as shown in FIG. 5, for a detector 61 provided with a rear collimator comprised of upper and lower baffle plates 64, 65, the vertical acceptance angle of the detector for back-scattered photons is reduced to viewing angle:

$$V=2\ \mathrm{arctangent}(d/2l) \qquad \text{(Equation 1.)}$$

where V is the angle or acceptance angle for back-scattered photons at rear surface 63 of detector 61, d is the vertical spacing between baffle plates 64, 65, and l is the length of the baffle plates. Referring still to FIG. 5, it may be seen that the vertical view angle or acceptance angle V for detector 61 provided with collimator 66 is bisected by a central perpendicular normal to rear face 63 of the detector, which is coincident with a transmitted ray 50. Therefore, acceptance angle V may be divided into components plus and minus $\alpha$ with respect to normal ray 50. And, as shown in FIG. 5, back-scattered rays such as ray 55 having an angle of incidence $\gamma$ (gamma) greater than $\alpha$ (alpha) are intercepted by an upper or lower collimator baffle plate 64, 65. As a result, those back-scattered rays 55 are attenuated before reaching detector 61, by absorption and/or scattering processes occurring in baffle plates 64, 65. Thus, providing detector 61 with a rear collimator 66 according to the present invention provides a method for reducing the intensity of back-scattered X-ray photons impinging on the detector.

Since the scattered photons such as those in back-scattered rays 55 represent noise rather than useful information indicative of target object features such as ray 67, which produced desired detector signals in detector 61, the use of collimator 66 increases the signal-to-noise ratio of signals output from the detector. The increased signal-to-noise ratio in turn results in images which contain less optical noise, and therefore enable object features to be discerned with greater contrast, resolution and clarity.

FIG. 6 illustrates an embodiment of the present invention which is suitable for use in attenuating back-scattered X-ray radiation incident upon an array of X-ray detectors.

As shown in FIG. 6, in an embodiment 70 of a back-scatter attenuation apparatus according to the present invention, for use with a detector array 71, which has a vertical column of individual detector elements 72, a vertical stack of parallel horizontally disposed collimator baffle plates 74 is disposed rearward from the array, at a distance b behind rear face 73 of the detectors. In a preferred configuration of this embodiment, the upper and lower edges of each detector element 71 are horizontally aligned with separate upper and lower collimator baffle plates 74; thus, for a columnar array 71 of N detectors, N+1 collimator baffle plates 74 are provided. The N+1 collimator baffle plates 74 together form an N-channel, single-axis rear collimator 76. The front edges 77 of collimator baffle plates 74 are preferably located a distance b rearward from rear surfaces 73 of detector elements to allow service access to detector array 71.

Figure 7:
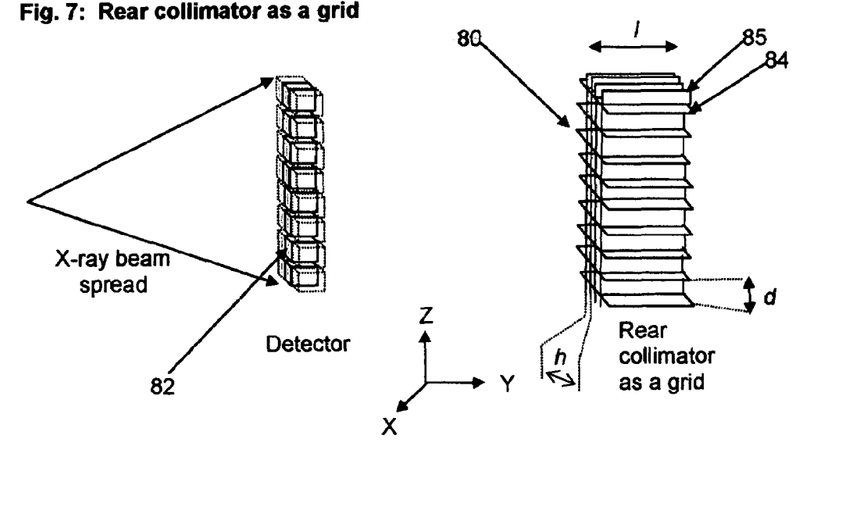
FIG. 7 is a perspective, partly diagrammatic view of an array of perpendicularly intersecting horizontal and vertical baffle plates arranged to form a matrix grid of two-axis collimator elements for attenuating X-ray radiation back-scattered onto an X-ray detector array.

FIG. 7 illustrates a "two-axis" embodiment of the present invention which attenuates X-ray radiation back-scattered onto a detector array from locations on either side of the array, as well as attenuating X-ray radiation which is back-scattered from locations above and below detector elements. As shown in FIG. 7, two-axis back-scatter attenuator apparatus 80 includes in addition to pairs of horizontally disposed, vertically spaced apart collimator baffle plates 84, located above and below each row of detector elements 82, a pair of vertically disposed baffle plates 85 which intersect the horizontally disposed collimator baffle plates.

Vertically disposed pair of collimator baffle plates 85 are aligned with opposite vertical edges of detector elements 82 in each column of the detector array. Thus positioned, each pair of vertical collimator baffle plates limits the unshadowed or unobstructed horizontal acceptance angle H of each detector element 82 in a column in a manner exactly analogous to the limitation of the vertical acceptance angle V as described above. Therefore, for a horizontal spacing h between each pair of vertical collimator baffle plates 85, the horizontal acceptance angle is given by:

$$H=2\ \mathrm{arctangent}(h/2l) \qquad \text{(equation 2).}$$

The total reduction in the amount of back-scattered X-rays resulting from the use of both vertical and horizontal pairs of collimator baffle plates 85, 84, is of course greater than that obtainable by using pairs of plates having only one orientation.

In a preferred configuration of the two-axis rear collimator 80 shown in FIG. 7, opposite vertical sides of each column of detectors 82 are aligned with separate vertical collimator baffle plates 85. Thus, for an array having M columns, M+1 vertical collimator baffle plates 85 are provided. Moreover, as stated above, for a column containing N detector elements, N+1 horizontal collimator baffle plates 84 are provided. With this arrangement, perpendicularly intersecting horizontal and vertical collimator baffle plates 84, 85 form a two-axis rear collimator 86 which has an egg-crate like grid structure that has MXN tubular, rectangular cross-section collimator channels which are analogous in function to optical lens hoods.

Figure 8:
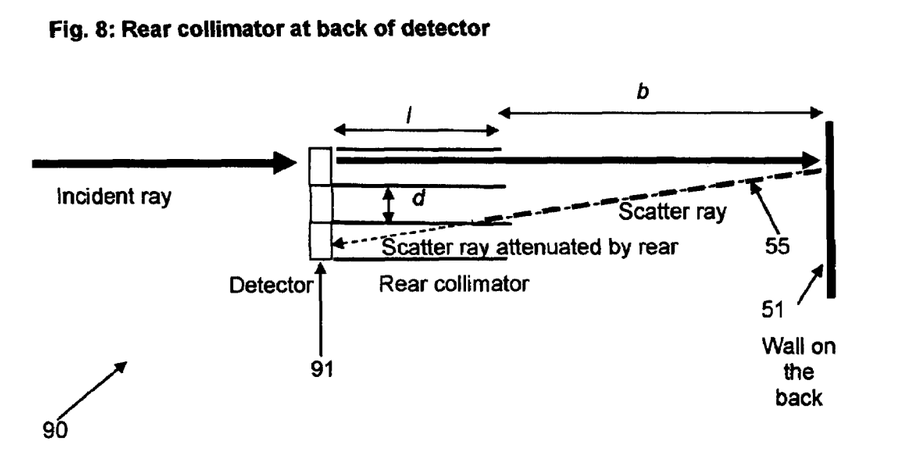
FIG. 8 is a diagrammatic view showing an embodiment of a back-scatter attenuator apparatus according to the present invention which includes a rear collimator that has baffles plates which protrude rearward from the rear surface of a detector array.
Figure 9:
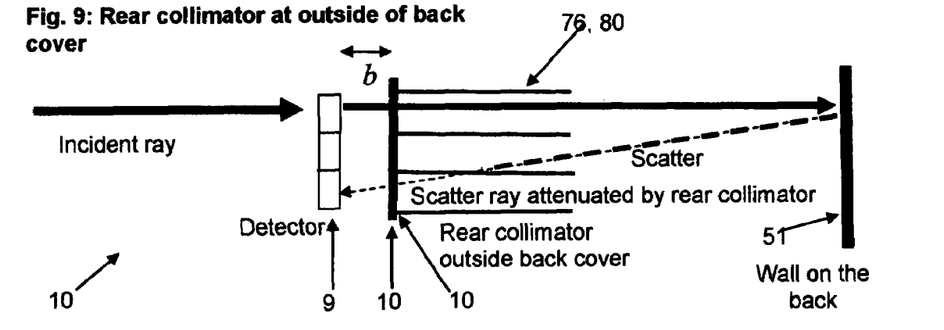
FIG. 9 is a diagrammatic view of another embodiment of the back-scatter attenuator collimator according to the present invention in which baffle plates protrude rearward from a support structure located rearward of a detector array.
Figure 10:
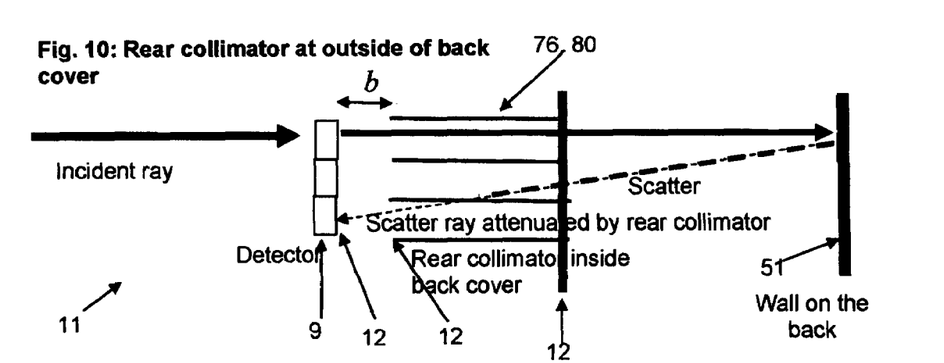
FIG. 10 is a diagrammatic view of another embodiment of a back-scatter attenuator collimator according to the present invention, which has baffle plates that protrude forward from a rear detector enclosure cover of a transmission X-ray radiography systems.

FIGS. 8-10 illustrate variations in the positions and orientations of collimators such as single-axis collimator 70 and double-axis collimator 80 according to the present invention.

Referring first to FIG. 8, in modification 90 a basic embodiment of a back-scatter attenuator method according to the present invention, a single-axis collimator 70 or a double-axis collimator 80 is positioned directly behind or contacting the rear surface of a detector array 91, to thereby attenuate back-scattered X-ray radiation rays 55 emanating from a back-stop 51.

FIG. 9 illustrates a second embodiment 100 of a method for attenuating back-scattered X-ray radiation according to the present invention, in which a single-axis rear collimator 70 or a double-axis rear collimator 80 is located a distance b behind a detector array 91. In the specific example of second embodiment 100 shown in FIG. 9, a rearward facing rear collimator 70 or 80 is attached to the rear surface 101 of a door 102 which provides access to an enclosure chamber (not shown) for detector array 91. Enclosures for X-ray radiation detectors such as array 91 are typically provided to shield photo-detectors coupled to X-ray radiation-responsive fluorescent scintillator plates from extraneous visible light, which would otherwise produce noise photo-currents.

FIG. 10 illustrates a third embodiment 110 of a method for attenuating back-scattered X-ray radiation according to the present invention. In the third embodiment 110, the orientation of rear collimator 70 or 80, of the type described above, is reversed from the orientation shown in the previous example embodiments, so that collimator baffle plates of the collimator protrude forward towards the rear surface of a detector array 92, from a location rearward of the detector array. In the specific example shown in FIG. 10, the baffle plates 84, as well as vertical baffle plates (not shown) protrude forward from inside surface 121 of rear detector enclosure door 102. Front edges 122 of baffle plates 74, 84 are preferably located a distance b rearward of rear surface 123 of detector 92 to allow service access to detector array 92.

Figure 11:
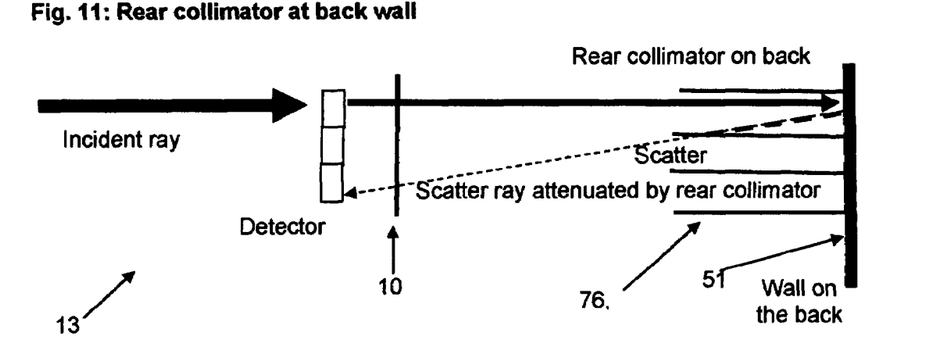
FIG. 11 is a diagrammatic view of another embodiment of a back-scatter attenuator collimator according to the present invention, which includes baffle plates that protrude forward from a back-stop wall.

FIG. 11 illustrates a fourth embodiment 130 of a method for attenuating back-scattered X-ray radiation according to the present invention. In the fourth embodiment 130, the orientation of collimator 70 ir 80, of the type described above, is forward facing as in the third embodiment shown in FIG. 10 and described above. However, collimator baffle plates of forward-facing rear collimator 70 or 80 are positioned at back-stop 51 rather than enclosure door 102 in this embodiment.

Figure 12:
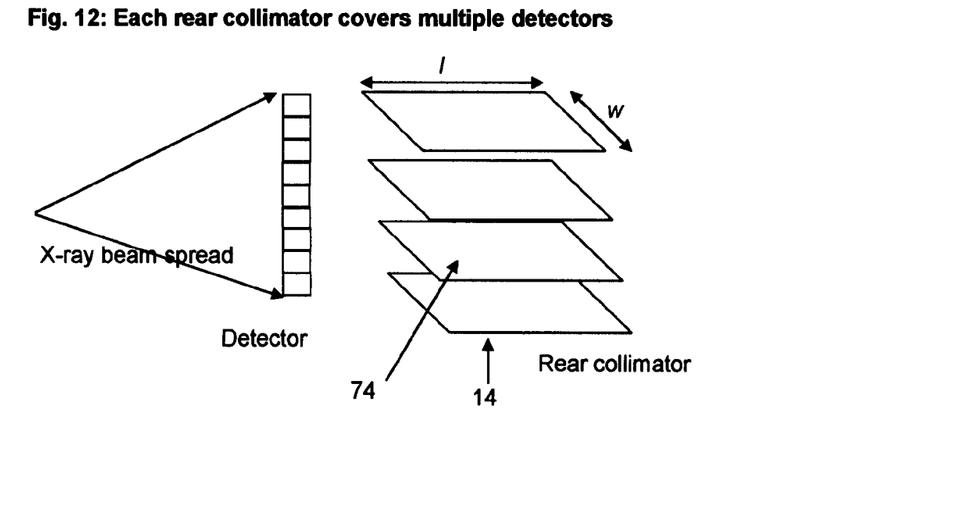
FIG. 12 is a partly diagrammatic perspective view of a back-scatter attenuating rear collimator for an X-ray radiation detector array which is similar to that shown in FIG. 6, but which utilizes fewer baffle plates by locating pairs of plates on opposite sides of a group of two or more detector rows rather than a single row of detectors.

FIG. 12 illustrates a variation 140 of embodiment 70 of back-scattered X-ray attenuator apparatus according to the present invention. Embodiment 140 is similar to embodiment 70 shown in FIG. 6 and described above, but utilizes fewer horizontal collimator baffle plates 74, locating pairs of collimator baffle plates above and below groups of detectors, rather than a single row of detectors. This arrangement reduces the cost and complexity of rear collimator 140 relative to rear collimator 70, but is less effective in attenuating back-scattered X-ray radiation, since the acceptance angles for receiving errant radiation are increased. The method of using pairs of baffle plates to baffle multiple adjacent rows of detectors is of course applicable to vertical baffle plates as well as horizontal baffle plates, and thus providing a lower cost variation of the two-axis grid collimator 80 shown in FIG. 7 and described above.

FIG. 13 illustrates another variation 150 of a back-scatter attenuating rear collimator for attenuating back-scattered X-ray radiation according to the present invention. Embodiment 150 is desirably used with detector arrays in which the spacing between individual detectors elements is relatively large. Such detector arrays enable X-ray radiation to pass unattenuated through gaps between adjacent detectors to impinge on a back-stop wall and produce thereat back-scattered radiation of relatively high intensity. In this situation, it is desirable to position rear collimator baffle plates according to the present invention in longitudinal, axial alignment with detector elements. Otherwise, unattenuated high intensity X-ray radiation would impinge on the forward edges of collimator baffle plates, which would thus become sources of relatively high intensity back-scattered X-ray radiation. Thus, as shown in FIG. 13, for a detector array 151 comprised of detector elements 152 spaced apart from one another by gaps 153, rear collimator baffle plates 154 are positioned rearward from the detector elements, with front and rear edges 155, 156 of each collimator plate axially aligned with a rear face 157 of a detector.

FIG. 14 illustrates another variation 160 of a back-scatter attenuating rear collimator for attenuating back-scattered X-ray radiation according to the present invention. Embodiment 160 is desirably used with detector arrays in which normal axes of individual detector elements are non-parallel, as for example, curved detector arrays used in CAT-Scan systems. Thus, as shown in FIG. 14, a detector array 161 is comprised of individual detector elements 162, the normal or longitudinal axes 163 perpendicular to front faces 164 of which are inclined with respect to one another at an angle Δ. Each detector element 162 has an upper side 165, a rear side 166 and a lower side 167. For this arrangement of detector elements 162, a back-scatter attenuating rear collimator 170 is provided which includes a plurality of flat collimator plates 174. In an embodiment of the invention which utilizes a pair of collimator plate 174 for each detector element 162, one of the collimator plates 174A would have an upper surface 175 which is parallel to upper side 165 of a detector element 162, while the other collimator plate 174B of the pair_would have a lower surface 177 which is parallel to lower side 167 of the detector element. This arrangement helps to insure that X-ray radiation which passes between detector elements travels rearward to a back-stop without impinging on a baffle plate 174A, 174B.

What is claimed is:

1. In an apparatus for obtaining an X-ray image of a target located between an X-ray radiation source and a back-stop object, said apparatus including one or more X-ray radiation detectors located rearward of said target and forward of said object, a method for reducing the intensity of X-ray radiation scattered onto a rear surface of a rearmost of said X-ray radiation detectors, said method comprising positioning at least a first X-ray radiation attenuating baffle plate between said rearmost X-ray radiation detector and said object, wherein said first baffle plate is axially aligned with a central longitudinal axis of said detector.

2. In an apparatus for obtaining an X-ray image of a target located between an X-ray radiation source and a back-stop object, said apparatus including one or more X-ray radiation detectors located rearward of said target and forward of said object, a method for reducing the intensity of X-ray radiation scattered onto a rear surface of a rearmost of said X-ray radiation detectors, said method comprising positioning at least a first-type X-ray radiation attenuating baffle plate between said rearmost X-ray radiation detector and said object, wherein said first-type baffle plate is axially aligned with a central longitudinal axis of a detector element of said one or more detectors.

3. An apparatus for reducing the intensity of X-ray radiation scattered onto a rear surface of a rearmost X-ray radiation detector located rearward of an X-ray radiation source and target and forward of a back-stop object, said apparatus comprising at least a first-type X-ray radiation attenuating baffle plate located between said rearmost X-ray radiation detector and said object, wherein said first-type baffle plate is axially aligned with a central longitudinal axis of a detector element of said detector.

4. The method of claim 1 wherein said first baffle plate is further defined as having a surface parallel to a longitudinal axis of said detector.

5. The method of claim 4 wherein said first baffle plate is further defined as having a tubular shape.

6. The method of claim 4 wherein said first baffle plate is further defined as having a surface adjacent to a first longitudinally disposed side of said detector.

7. The method of claim 6 further including positioning a second baffle plate adjacent to a second longitudinally disposed side of said detector.

8. The method of claim 7 wherein said second baffle plate is further defined as having a surface parallel to said second longitudinally disposed side of said detector.

9. The method of claim 8 further including positioning a third baffle plate adjacent to a third longitudinally disposed side of said detector.

10. The method of claim 9 wherein said third baffle plate is further defined as having a surface parallel to said third longitudinally disposed side of said detector.

11. The method of claim 10 further including positioning a fourth baffle plate adjacent to a fourth longitudinally disposed side of said detector.

12. The method of claim 11 wherein said fourth baffle plate is further defined as having a surface parallel to said fourth longitudinally disposed side of said detector.

13. The method of claim 12 wherein said third and fourth baffle plates are further defined as being oriented perpendicularly to said first and second baffle plates.

14. The method of claim 1 wherein said first baffle plate is further defined as being composed at least partially of an X-ray radiation absorbing material.

15. The method of claim 1 wherein said first baffle plate is further defined as being composed at least partially of a metal.

16. The method of claim 1 wherein said first baffle plate is further defined as composed at least partially of a metal having an atomic number Z at least as high as that of iron.

17. The method of claim 2 wherein said first-type baffle plate is further defined as having a tubular shape.

18. The method of claim 2 wherein said first-type baffle plate is further defined as being one of a plurality of first-type baffle plates, each one of which is axially aligned with a central longitudinal axis at a separate detector element of said array.

19. The method of claim 2 wherein said first-type baffle plate is further defined as being one of a plurality of pairs of first-type baffle plates, opposite members of each said pair being located in approximate longitudinal alignment with a first pair of opposite longitudinally disposed sides of a detector element of said array.

20. The method of claim 19 further including the step of positioning a second-type baffle plate between said rear surface of said detector array and said object.

21. The method of claim 20 wherein said second-type of baffle plate is axially aligned with a central longitudinal axis of a detector element of said array.

22. The method of claim 20 wherein said second-type baffle plate is further defined as being one of a plurality of second-type baffle plates, each one of which is axially aligned with a central longitudinal axis of a separate detector element of said array.

23. The method of claim 20 wherein said second-type baffle plate is further defined as being one of a plurality of pairs of second-type baffle plates, opposite members of each said pair being disposed transversely to said first-type baffle plates.

24. The method of claim 23 wherein opposite members of each of said pair of second-type baffle plates are further defined as being located in approximate longitudinal alignment with a second pair of opposite longitudinally disposed sides of a detector element of said array.

25. The method of claim 20 wherein at least one of said first-type and second-type baffle plates is further defined as being composed at least partially of an X-ray radiation absorbing material.

26. The method of claim 20 wherein at least one of said first-type and second-type baffle plates is further defined as being composed at least of a metal.

27. The method of claim 20 wherein at least one of said first-type and second-type baffle plates is further defined as being composed at least partially of a metal having an atomic number Z at least as high as that of iron.

28. The apparatus of claim 3 wherein said X-ray radiation detector is further defined as being an element of an array of detector elements.

29. The apparatus of claim 28 wherein said first-type baffle plate is further defined as being one of a plurality of first-type baffle plates, each one of which is axially aligned with a central longitudinal axis of a separate detector element of said array.

30. The apparatus of claim 29 wherein said first-type baffle plate is further defined as having a tubular shape.

31. The apparatus of claim 28 wherein said first-type baffle plate is further defined as being one of a plurality of pairs of first-type baffle plates, opposite members of each said pair being located in approximate longitudinal alignment with a first pair of opposite longitudinally disposed sides of a detector element of said array.

32. The apparatus of claim 31 further including a second-type X-ray radiation attenuating baffle plate located between said rear side of said X-ray radiation detector and said object.

33. The apparatus of claim 32 wherein said second-type of baffle plate is axially aligned with a central longitudinal axis of a detector element of said array.

34. The apparatus of claim 32 wherein said second-type baffle plate is further defined as being one of a plurality of second-type baffle plates, each one of which is axially aligned with a central longitudinal axis of a separate detector element of said array.

35. The apparatus of claim 32 wherein said second-type baffle plate is further defined as being one of a plurality of pairs of second-type baffle plates, opposite members of each said pair being disposed transversely to said first-type baffle plates.

36. The apparatus of claim 35 wherein opposite members of each of said pair of second-type baffle plates is further defined as being located in approximate longitudinal alignment with a second pair of opposite longitudinally disposed sides of a detector element of said array.

37. The apparatus of claim 32 wherein at least one of said first-type and second-type baffle plates is further defined as being composed at least partially of an X-ray radiation absorbing material.

38. The method of claim 32 wherein at least one of said first-type and second-type baffle plates is further defined as being composed at least partially of a metal.

39. The method of claim 32 wherein at least one of said first-type and second-type baffle plates is further defined as being composed at least partially of a metal having an atomic number Z at least as high as that of iron.

* * * * *